US007599744B2

(12) United States Patent  (10) Patent No.: US 7,599,744 B2
Giordano et al.  (45) Date of Patent: Oct. 6, 2009

(54) TRANSCUTANEOUS ENERGY TRANSFER PRIMARY COIL WITH A HIGH ASPECT FERRITE CORE

(75) Inventors: James R. Giordano, Milford, OH (US); Daniel F. Dlugos, Jr., Morrow, OH (US); William L. Hassler, Jr., Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 581 days.

(21) Appl. No.: 10/876,313

(22) Filed: Jun. 24, 2004

(65) Prior Publication Data

US 2005/0288742 A1  Dec. 29, 2005

(51) Int. Cl.
*A61N 1/00* (2006.01)
(52) U.S. Cl. ........................................................ 607/61
(58) Field of Classification Search .................. 607/33, 607/61, 2, 34
See application file for complete search history.

(56) References Cited

U.S. PATENT DOCUMENTS

| | | | |
|---|---|---|---|
| 3,727,616 | A | 4/1973 | Lenzkes |
| 3,867,950 | A | 2/1975 | Fischell et al. |
| 4,096,866 | A | 6/1978 | Fischell |
| 4,281,664 | A | 8/1981 | Duggan |
| 4,361,153 | A | 11/1982 | Slocum et al. |
| 4,441,210 | A | 4/1984 | Hochmair et al. |
| 4,581,018 | A | 4/1986 | Jassawalla et al. |
| 4,611,598 | A | 9/1986 | Hortmann et al. |
| 4,665,896 | A | 5/1987 | LaForge et al. |
| 4,681,111 | A | 7/1987 | Silvian |
| 5,109,843 | A | 5/1992 | Melvin et al. |
| 5,350,413 | A | 9/1994 | Miller |
| 5,507,737 | A | 4/1996 | Palmskog |
| 5,690,693 | A | 11/1997 | Wang et al. |

(Continued)

FOREIGN PATENT DOCUMENTS

GB  2 239 802  7/1991

(Continued)

OTHER PUBLICATIONS

USPTO Office Action for U.S. Appl. No. 10/876,058, dated May 23, 2006.

(Continued)

*Primary Examiner*—Carl H. Layno
*Assistant Examiner*—Jon-Eric C. Morales
(74) *Attorney, Agent, or Firm*—Frost Brown Todd LLC (57) ABSTRACT

Adjustable gastric band implants contain a hollow elastomeric balloon with fixed end points encircling a patient's stomach just inferior to the esophago-gastric junction. These balloons can expand and contract through the introduction of saline solution into the balloon. In current bands, this saline solution must be injected into a subcutaneous port with a needle to reach the port located below the skin surface. The port communicates hydraulically with the band via a catheter. As an alternative to using a percutaneously accessed injection port, a system for regulating the flow of saline that is totally implanted may rely upon bi-directionally pumping fluid from an implant device. This system instead transfers AC magnetic flux energy from an external primary coil to a secondary coil that powers the pump in the implanted reservoir. A magnetically permeable rod centered within the primary coil increases power coupled to the secondary coil.

12 Claims, 3 Drawing Sheets

U.S. PATENT DOCUMENTS

| | | | |
|---|---|---|---|
| 5,715,837 A * | 2/1998 | Chen | 128/899 |
| 5,733,313 A | 3/1998 | Barreras, Sr. et al. | |
| 5,741,315 A | 4/1998 | Lee et al. | |
| 5,741,316 A * | 4/1998 | Chen et al. | 607/61 |
| 5,938,669 A | 8/1999 | Klaiber et al. | |
| 5,974,873 A | 11/1999 | Nelson | |
| 5,991,664 A | 11/1999 | Seligman et al. | |
| 6,058,330 A | 5/2000 | Borza | |
| 6,102,678 A | 8/2000 | Peclat | |
| 6,115,636 A | 9/2000 | Ryan | |
| 6,208,894 B1 | 3/2001 | Schulman et al. | |
| 6,315,769 B1 | 11/2001 | Peer et al. | |
| 6,324,431 B1 * | 11/2001 | Zarinetchi et al. | 607/61 |
| 6,327,504 B1 | 12/2001 | Dolgin et al. | |
| 6,366,817 B1 | 4/2002 | Kung | |
| 6,430,444 B1 | 8/2002 | Borza | |
| 6,463,329 B1 | 10/2002 | Goedeke | |
| 6,482,177 B1 | 11/2002 | Leinders | |
| 6,505,077 B1 | 1/2003 | Kast et al. | |
| 6,542,350 B1 | 4/2003 | Rogers | |
| 6,585,763 B1 * | 7/2003 | Keilman et al. | 623/1.42 |
| 6,889,087 B2 | 5/2005 | Moore | |
| 6,895,281 B1 | 5/2005 | Amundson et al. | |
| 7,016,733 B2 | 3/2006 | Dublin et al. | |
| 7,092,762 B1 | 8/2006 | Loftin et al. | |
| 7,191,007 B2 | 3/2007 | Desai et al. | |
| 7,225,032 B2 | 5/2007 | Schmeling et al. | |
| 7,286,881 B2 | 10/2007 | Schommer et al. | |
| 2002/0055763 A1 * | 5/2002 | Zarinetchi et al. | 607/61 |
| 2002/0087204 A1 | 7/2002 | Kung et al. | |
| 2002/0177884 A1 * | 11/2002 | Ahn et al. | 607/61 |
| 2004/0095333 A1 | 5/2004 | Morag et al. | |
| 2004/0138725 A1 * | 7/2004 | Forsell | 607/61 |
| 2005/0288739 A1 | 12/2005 | Hassler, Jr. et al. | |
| 2005/0288740 A1 | 12/2005 | Hassler et al. | |
| 2005/0288741 A1 | 12/2005 | Hassler et al. | |
| 2006/0155347 A1 | 7/2006 | Forsell | |

FOREIGN PATENT DOCUMENTS

| | | |
|---|---|---|
| WO | WO 98/11942 | 3/1998 |
| WO | WO 00/24456 | 5/2000 |
| WO | WO 00 72899 | 12/2000 |

OTHER PUBLICATIONS

USPTO Office Action for U.S. Appl. No. 10/876,058, dated Dec. 6, 2006.

USPTO Office Action for U.S. Appl. No. 10/876,058, dated Jul. 20, 2007.

USPTO Office Action for U.S. Appl. No. 10/876,307, dated Mar. 22, 2007.

USPTO Office Action for U.S. Appl. No. 10/876,307, dated Oct. 15, 2007.

USPTO Office Action for U.S. Appl. No. 10/876,058, dated Jan. 8, 2008.

Examination Report dated Jul. 29, 2008 for Application No. EP 05 253 917.8.

European Search Report dated Sep. 30, 2005 for Application No. EP05253917.

European Search Report dated Oct. 19, 2005 for Application No. EP05253919.

European Search Report dated Oct. 21, 2005 for Application No. EP05253920.

Examination Report dated Jul. 17, 2008 for Application No. EP05253919.

Examination Report dated Oct. 27, 2006 for Application No. EP05253920.

Examination Report dated Apr. 5, 2007 for Application No. EP05253920.

Examination Report dated Dec. 14, 2007 for Application No. EP05253920.

* cited by examiner

TRANSCUTANEOUS ENERGY TRANSFER PRIMARY COIL WITH A HIGH ASPECT FERRITE CORE

CROSS REFERENCE TO RELATED APPLICATIONS

The present application is related to four co-pending and commonly-owned applications filed on even date herewith, the disclosure of each being hereby incorporated by reference in their entirety, entitled respectively:

"MEDICAL IMPLANT HAVING CLOSED LOOP TRANSCUTANEOUS ENERGY TRANSFER (TET) POWER TRANSFER REGULATION CIRCUITRY" to William L. Hassler, Jr., Ed Bloom, Ser. No. 10/876,038;

"SPATIALLY DECOUPLED TWIN SECONDARY COILS FOR OPTIMIZING TRANSCUTANEOUS ENERGY TRANSFER (TET) POWER TRANSFER CHARACTERISTICS" to Reshai Desai, William L. Hassler, Jr., Ser. No. 10/876,057, now U.S. Pat. No. 7,191,007;

"LOW FREQUENCY TRANSCUTANEOUS TELEMETRY TO IMPLANTED MEDICAL DEVICE" to William L. Hassler, Jr., Ser. No. 10/876058; and "LOW FREQUENCY TRANSCUTANEOUS ENERGY TRANSFER TO IMPLANTED MEDICAL DEVICE" to William L. Hassler, Jr., Daniel F. Dlugos, Jr., Ser. No. 10/876,307.

FIELD OF THE INVENTION

The present invention relates, in general, to medically implantable devices that receive transcutaneous energy transfer (TET), and more particularly, such implant devices that optimize power transfer.

BACKGROUND OF THE INVENTION

In a TET system, a power supply is electrically connected to a primary coil that is external to a physical boundary, such as the skin of the human body. A secondary coil is provided on the other side of the boundary, such as internal to the body. With a subcutaneous device, both the primary and secondary coils are generally placed proximate to the outer and inner layers of the skin. Energy is transferred from the primary coil to the secondary coil in the form of an alternating magnetic field. The secondary coil converts the transferred energy in the AC magnetic field to electrical power for the implant device, which acts as a load on the secondary coil.

In a TET system, the primary and secondary coils are placed on separate sides of the boundary or skin. This separation typically results in variations in the relative distance and spatial orientation between the coils. Variations in the spacing can cause changes in the AC magnetic field strength reaching the secondary coil, in turn causing power fluctuations and surges in the implant device. Implant devices, such as those used in medical applications, usually rely upon a microcontroller to perform various functions. These microcontrollers require a consistent, reliable power source. Variations in the supplied power, such as sudden changes in voltage or current levels, may cause the device to perform erratically or fail to function at all. Accordingly, one issue associated with conventional TET systems is that the physical displacement of either the primary or secondary coils from an optimum coupling position may cause an unacceptable effect on the output power supplied to the implanted device.

As an example of an implantable device that may benefit from use of TET is an artificial sphincter, in particular an adjustable gastric band that contains a hollow elastomeric balloon with fixed end points encircling a patient's stomach just inferior to the esophago-gastric junction. These balloons can expand and contract through the introduction of saline solution into the balloon. In generally known adjustable gastric bands, this saline solution must be injected into a subcutaneous port with a syringe needle to reach the port located below the skin surface. The port communicates hydraulically with the band via a catheter. While effective, it is desirable to avoid having to adjust the fluid volume with a syringe needle since an increased risk of infection may result, as well as inconvenience and discomfort to the patient.

To that end, in the below-referenced co-pending applications, an implanted infuser device regulates the flow of saline without requiring injection into the subcutaneous port. This system instead transfers AC magnetic flux energy from an external primary coil to a secondary coil that powers the pump in the implant connected to the gastric band within the abdomen.

Although such TET powering of an implant, such as to recharge batteries, is a generally known procedure, using TET for an artificial sphincter system, such as an adjustable gastric band, presents a number of challenges. Adjustable gastric bands are most beneficial to patients that are morbidly obese. Providing a secure location to subcutaneously attach an implant that presents a reduced incident of discomfort often means that the implant is under a thick layer of skin and adipose tissue. A major challenge in using TET thus is transferring magnetic energy between the primary and secondary coils through this thick layer of tissue, which thus reduces the effective amount of power transferred to the implant.

It is also generally known to include a magnetic shield across an external side of a primary coil used in TET powering of an artificial heart, such as described in U.S. Pat. No. 6,389,318. Such magnetic shields are generally a flat disk that overlays the top and sides of the primary coil for the purpose of shielding from other conductors in the external environment. Perforations are included for ventilation since such primary coils are continually positioned on the patient. To be conformal, a preferred material is silicon impregnated with ferrite powder so that its low magnetic loss serves as a back plane that reflects magnetic energy from the primary coil. While providing advantages for external sources of electromagnetic interference, such shields are not believed to substantially assist in directing the magnetic flux to the secondary coil of an implanted medical device.

While the shield described in U.S. Pat. No. 6,389,318 provided some shaping of the magnetic flux from the primary coil, one undesirable characteristic thereof was that the magnetic flux was flattened, providing less efficient power coupling to deeply embedded implantable devices. In the application described for artificial hearts, the secondary coil was near to the surface of the patient's skin and thus this apparently did not pose a problem.

In U.S. Pat. No. 5,715,837, enhancing the effectiveness of TET was addressed by increasing the magnetic permeability of the flux path through the dermis of the patient by implanting soft iron pellets therein. It would be undesirable to implant metal pellets for a number of reasons. First, in the morbidly obese patient, it may require a significant amount of pellets to seed the flux path. Second, the patient may object to this permanent implantation. Third, being ferrous objects, tissue damage or discomfort may result if the patient were in the presence of a strong magnetic field typical of a Magnetic Resonance Imaging (MRI) machine. Fourth, these ferrous objects would create artifacts that would hamper diagnostic imaging such as MRI and CT. Fifth, the chemical or physical properties of these pellets may have a deleterious effect on the dermis.

It is further inconvenient to shape the magnetic flux as described in U.S. Pat. No. 5,715,837 with opposing horseshoe shaped ferrite cores insofar as it is desirable to eliminate such mass from an implanted device to make it smaller. In addition, it is further desirable to eliminate materials that respond to strong magnetic fields, as mentioned with regard to soft iron pellets or a partially exposed, implanted ferrite core.

In U.S. Pat. No. 5,279,292, a charging system for an implantable hearing aid or tinnitus masker included a receiving coil that is implanted under the skin in mastoid. The receiving coil included a ferrite core that projected outward through the skin. Thus, a transmitting coil is placed over the exposed end of the ferrite core, mechanically aligning the primary coil and enhancing magnet coupling to the receiving core. Due to the relatively small amount of power transferred, the ferrite core is described as being small and unobtrusive and being hidden behind the external ear. However, it is undesirable to have an exposed implant that tends to allow infections. In addition, use of a transformer instead of TET as in this application also makes the implant not compatible with MRI machines.

Consequently, a significant need exists for enhancing TET power transfer from a primary coil through the dermis of a patient to an implanted device that contains a secondary coil.

BRIEF SUMMARY OF THE INVENTION

The invention overcomes the above-noted and other deficiencies of the prior art by providing a transcutaneous energy transfer (TET) system that includes a primary coil having a magnetic flux shaping member centered within its circular diameter, thereby forming a toroidal magnetic flux field with an implanted secondary coil in a patient that is more elliptical in cross section. Thereby, greater power coupling efficiency is achieved, enabling medical implants to be placed at greater depths. Thus, applications such as remotely controllable adjustable gastric bands for the morbidly obese may be used without having to resort to inconveniently high power levels nor to having to embed separate secondary coils near the surface of the dermal layer.

In one aspect of the invention, an external TET device includes a circular power coil that is energized at a resonant frequency to provide magnetic flux to a secondary coil of an implanted medical device. A very highly magnetically permeable member is centered within the primary coil to shape a resulting magnetic field into a more elliptical toroidal shape with respect to its longitudinal axis.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
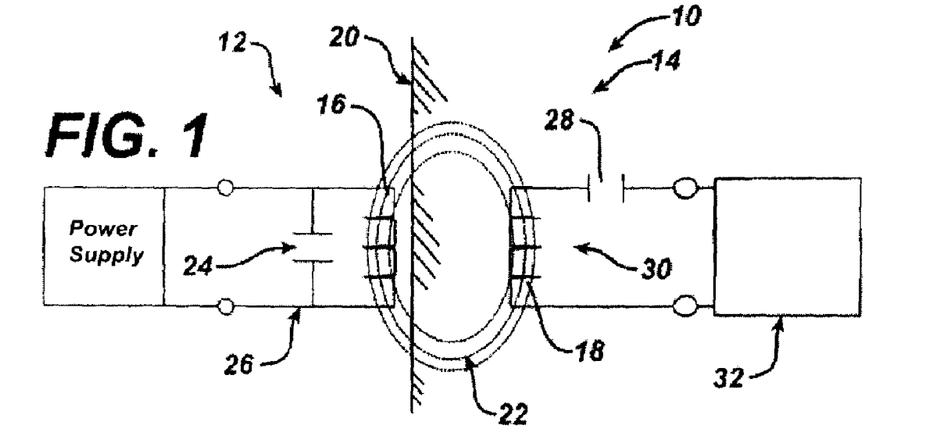
FIG. 1 is a circuit block diagram of a transcutaneous energy transfer (TET) system coupled to a power supply.

Referring now to the drawings in detail, wherein like numerals indicate the same elements throughout the views, FIG. 1 depicts the relationship between a transcutaneous energy transfer (TET) system 10 that has an external device 12 and an implanted device 14. The external device 12 includes a primary coil 16 that is external to a patient. The implanted device 14 includes a secondary coil 18 that inductively receives power from the primary coil 16 transcutaneously through a dermal layer 20 of the patient, as depicted by alternating current (AC) magnetic flux lines 22. The primary coil 16 is connected in parallel with capacitance 24 to form a resonant parallel tank circuit 26. The AC magnetic flux 22 generated by the resonant tank circuit 26 is collected by secondary coil 18, which is connected in series with a secondary capacitance 28 to form a secondary resonant series tuned tank circuit 30, which delivers power to implant circuitry 32.

As an example of an implanted device 14 that would benefit from TET is an infuser device, described in greater detail in the referenced applications, that regulates the amount of fluid dispensed bi-directionally into an expandable gastric band following implantation of the band during weight reduction surgery. The TET system 10 may consist of the primary coil 16 occasionally placed outside a patient's abdomen when adjustment of the gastric band is desired and the secondary coil 18 within an infuser implanted device 14 that has been anchored subcutaneously on a layer of muscular fascia within the patient. The illustrative primary coil 16, having an outer diameter (OD) of about five (5) inches (13 cm) and consisting of one hundred two (102) turns of litz wire made up of one hundred (100) individually insulated thirty (30)-gauge magnet wires, is connected in parallel with 9.2 microfarads of capacitance, creating a parallel tuned resonant tank circuit with a very high Q. The secondary coil 18 is connected in series with a capacitor 28 forming a series tuned resonant tank circuit and is activated by receiving AC magnetic flux energy from the primary coil 16. The two tuned tank circuits 24, 30 are tuned to the same frequency for optimal power transfer.

Implantable, bi-directional infusing devices that would benefit from enhanced TET powering and telemetry are disclosed in four co-pending and co-owned patent applications filed on May 28, 2004, the disclosure of which are hereby incorporated by reference in their entirety, entitled (1) "PIEZO ELECTRICALLY DRIVEN BELLOWS INFUSER FOR HYDRAULICALLY CONTROLLING AN ADJUSTABLE GASTRIC BAND" to William L. Hassler, Jr., Ser. No. 10/857,762; (2) "METAL BELLOWS POSITION FEED BACK FOR HYDRAULIC CONTROL OF AN ADJUSTABLE GASTRIC BAND" to William L. Hassler, Jr., Daniel F. Dlugos, Jr., Rocco Crivelli, Ser. No. 10/856,971; (3)

"THERMODYNAMICALLY DRIVEN REVERSIBLE INFUSER PUMP FOR USE AS A REMOTELY CONTROLLED GASTRIC BAND" to William L. Hassler, Jr., Daniel F. Dlugos, Jr., Ser. No. 10/857,315; and (4) "BI-DIRECTIONAL INFUSER PUMP WITH VOLUME BRAKING FOR HYDRAULICALLY CONTROLLING AN ADJUSTABLE GASTRIC BAND" to William L. Hassler, Jr., Daniel F. Dlugos, Jr., Ser. No. 10/857,763.

Figure 2:
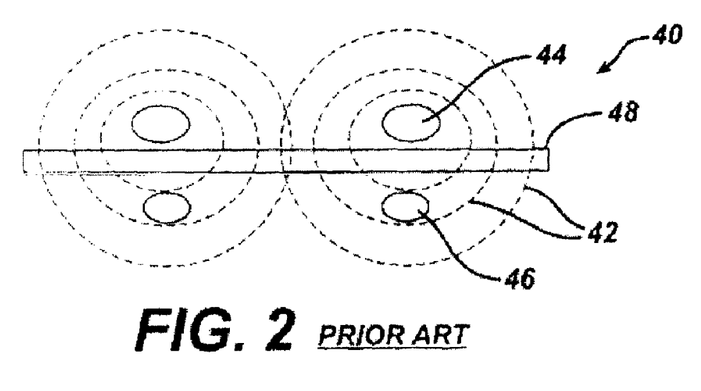
FIG. 2 is a magnetic flux diagram of a prior art TET system having a primary coil and implanted secondary coil.

FIG. 2 shows a generally known TET device 40 that achieves a magnetic field, depicted as shallow flux lines 42 between parallel primary and secondary TET coils 44, 46. Primary coil 44 transfers magnetic flux 42 through an abdominal wall 48 to the secondary coil 46. Due to losses and the shape of the magnetic field 42, the secondary coil 46 is constrained to be placed relatively close to the exterior of the abdominal wall 48 since the magnetic field 42 has a circular toroidal shape that does not achieve optimal energy transfer between the two coils 44, 46.

Figure 3:
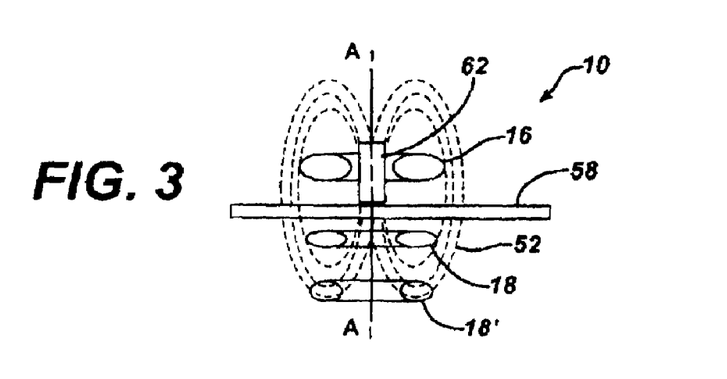
FIG. 3 is a magnetic flux diagram of a TET system having a magnetic flux conducting core centered within the primary coil to shape a resultant magnetic flux.

FIG. 3 depicts the TET system 10 of FIG. 1 that advantageously shapes a TET magnetic field 52 into an elliptical shape that more efficiently operates through an abdominal wall 58 of a patient. Thus, at an implanted depth equivalent to the prior art secondary coil 18, more power is transferred. Alternatively, a secondary coil 18' may be placed at a greater depth for more secure attachment and enhanced patient comfort yet be able to receive sufficient power. In particular, a ferrite rod 62 aligned at a circular center of an external primary coil 16 extends along a center axis A-A of the primary coil, shaping the magnetic flux 52 into an elliptical toroidal shape, and causing an increase in flux density within the secondary coil 18.

Figure 4:
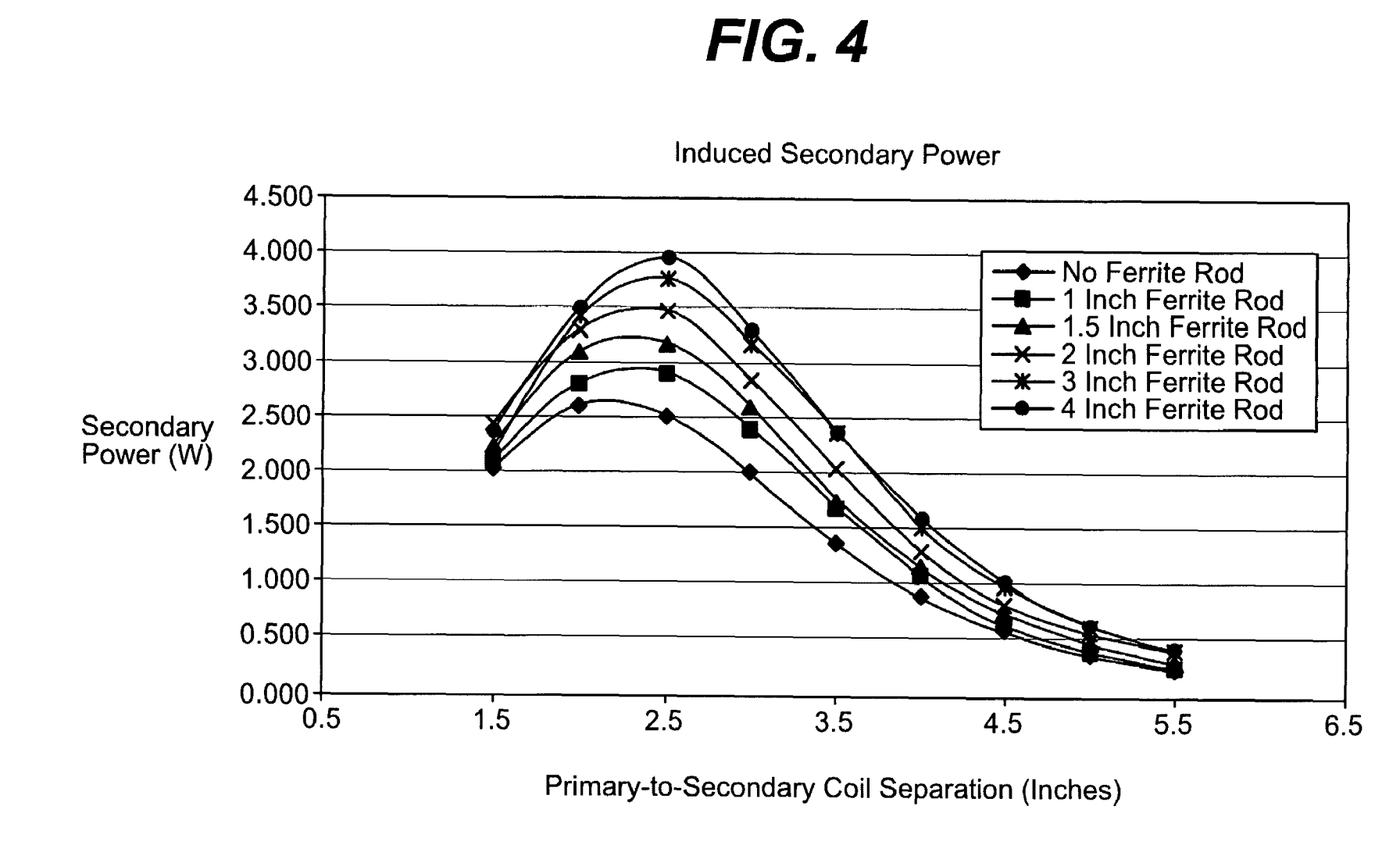
FIG. 4 is a plot of power induced in a secondary coil by various lengths of a flux shaping core in the primary coil and different depths of separation between primary and secondary coils.

This enhanced power transfer is depicted in FIG. 4, showing the difference in energy transfer efficiency before and after placement of the ferrite cores 62 of different lengths into the primary coil 16. It was shown that a benefit existed for additional power received in the secondary circuit for separation distances of 1.5 to 5.5 inches by the inclusion of a core of lengths between 1 to 4 inches. Extrapolating from the results indicates that some benefit would be appreciated by a shorter length of a core, if constrained by available clearance considerations. In addition, longer lengths of a core may be used to obtain additional power coupling efficiencies.

To achieve the greatest energy transfer efficiency, a highly magnetically permeable ferrite core 62 has been placed within the primary coil 16. As stated previously, we determined that the optimum core 62 is of a long, skinny design. Testing indicates that a ferrite core rod 62 with a length of about 3 inches and a width of about 0.75 inches is the optimal size for the given primary coil 16 at which energy transfer is at its most efficient without going into magnetic saturation or wasting energy in the form of eddy current losses within the core 62.

With the long and slender core design, most of the magnetic flux is drawn toward the ferrite core 62, causing the field to collapse radially into the core 62 and changing the shape of the field 52 from circular to elliptical. This effect leads to an increase in the flux density within the secondary coil 18. In an exemplary version, a ferrite core of 3 inches length and 0.75 inches diameter was placed within the center of a 5 inch diameter primary coil 16 of the transcutaneous energy transfer (TET) system 10. With the addition of this core 62, the power coupling efficiency to the secondary TET coil was increased by up to 55%.

Laminated Steel Core.

Figure 5:
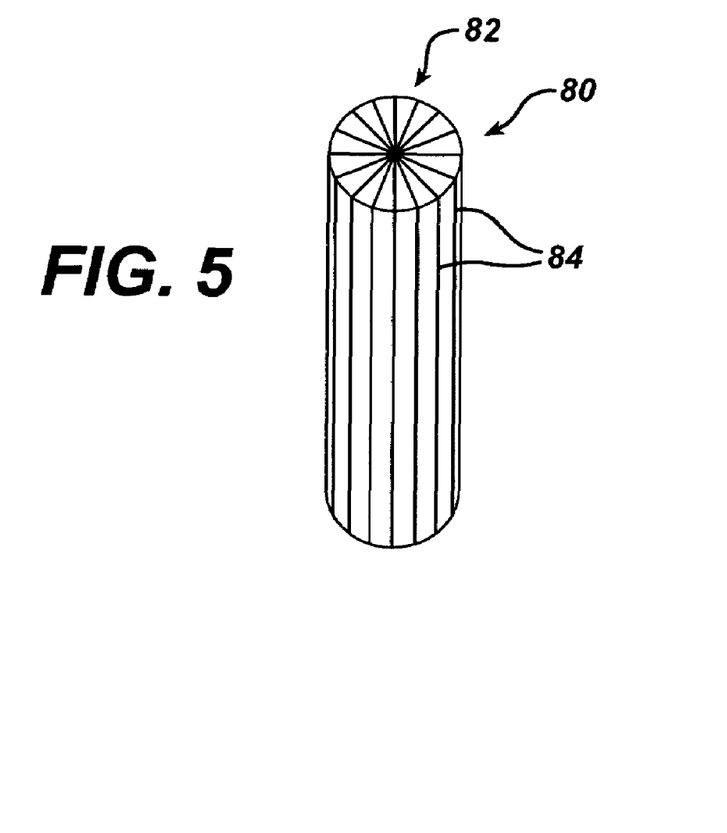
FIG. 5 is a an alternative magnetic flux shaping core formed from a slender steel rod divided into sixteen sections electrically isolated along their length, each having a "pie-shaped" cross section.

In FIG. 5, as an alternative to a ferrite rod core, a cylindrical core 80 was made of a Carpenter Steel 430 FR stainless steel. The core was 1.25 inches in diameter, and 3.0 inches long. This core was longitudinally segmented into 16 different "pie" shaped 82 radial portions that were electrically isolated from each other by a high temperature epoxy (Duralco 4525) 84. This laminating process was done in order to minimize the eddy current losses in the core 80, while trying to maximize the magnetic flux carrying capability of the core. The magnetic permeability of the steel is actually half of the ferrite materials, but the saturation flux density is around four times higher, allowing for much more magnetic flux to pass through the same sized core.

"Pot" Core.

Figure 6:
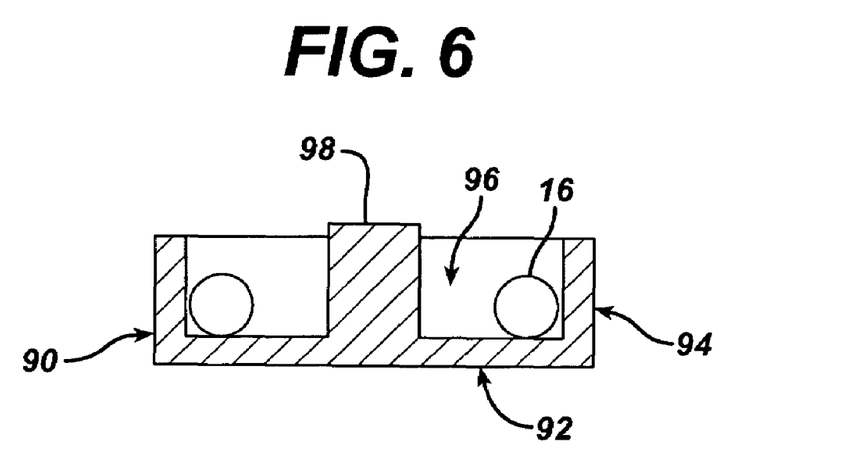
FIG. 6 is a further alternative magnetic flux shaping core depicted as a ferrite pot core shaped as a disk with a ring groove formed in a bottom surface to receive a primary coil.

In FIG. 6, as a further alternative to a ferrite rod core, a ferrite pot core 90 was made to reshape the magnetic field so as to increase the range, and/or power coupling of the TET system 10. The pot core 90 has a disk portion 92 that covers an exteriorly facing side of the primary coil 16. A cylindrical flange 94 is inwardly directed toward the patient attached to the circumference of the disk portion 92, thereby assisting electromagnetic interference shielding of the primary coil 16 that resides within a circular groove 96, which also defines a central rod 98. The circular groove 96 opens toward an inward face of the pot core 90 that would be placed toward the patient. The central rod 98 shapes the magnetic field into a more elliptical toroidal shape as previously discussed. The pot core 90 may be visualized by taking an E shape and revolving it about the centerline of the center prong of the E. The material thickness of the pot core may be minimized in order to reduce the eddy current losses within the core without causing the core to go into magnetic saturation.

By virtue of the foregoing, the elliptical shape of the magnetic field increases the coupling efficiency between the primary and secondary TET coils. Increased coupling efficiency between the coils reduces the amount of power required from the primary coil and also increases the range at which the external primary coil can be separated from the subcutaneous secondary coil, an important consideration in facilitating weight reduction surgery where thick abdominal walls are typically encountered.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, it will become readily apparent to those skilled in the art that the above invention has equal applicability to other types of implantable bands. For example, bands are used for the treatment of fecal incontinence. One such band is described in U.S. Pat. No. 6,461,292, which is hereby incorporated herein by reference. Bands can also be used to treat urinary incontinence. One such band is described in U.S. patent application 2003/0105385, which is hereby incorporated herein by reference. Bands can also be used to treat heartburn and/or acid reflux. One such band is described in U.S. Pat. No. 6,470,892, which is hereby incorporated herein by reference. Bands can also be used to treat impotence. One such band is described in U.S. Patent Application Publ. No. 2003/0114729, which is hereby incorporated herein by reference.

As another example, it should be appreciated that a shaping magnetic flux with a highly magnetically permeable member centered within the primary coil enhances transcutaneous energy transfer used for telemetry in addition to or in the alternative to TET for powering an implanted device. For instance, a primary coil may be used intermittently for telemetry sending or receiving or include a primary telemetry coil in addition to a primary power coil.

As yet a further example, it should be appreciated that in applications that require a relatively low amount of power transfer and/or only occasional periods of time for TET, materials chosen for the core may include those subject to eddy currents and heating. Alternatively, thermally insulating materials may be included to protect the skin of the patient from discomfort or injury.

What is claimed is:

1. A transcutaneous energy transfer device for transferring energy from an external device located outside of a patient's skin to an internal device implanted below the patient's skin, the transcutaneous energy transfer device comprising:

an external device configured to be placed adjacent to skin on the exterior of a patient and to transmit energy into the patient, the external device comprising:
i) a primary transmitter coil comprising at least one wire wrapped around a primary central axis of the primary transmitter coil into a toroid shape encircling the primary central axis, the toroid shape having:
a) an exterior primary surface defined by an elliptical cross section of the toroid shape rotated about the primary central axis,
b) a central gap between the exterior primary surface and the primary central axis,
c) a primary minimum diameter where the primary surface of the toroid shape is closest to the primary central axis, and
d) a primary coil height, wherein the primary coil height is less than the primary minimum diameter;
ii) an elongate member positioned within the central gap of the primary transmitter coil and having a longitudinal axis, wherein the elongate member comprises a plurality of wedge-shaped slender components, wherein each slender component of the plurality of slender components is attached to an adjacent slender component of the plurality of slender components, the elongate member further comprising an electrically insulating material positioned between each of the adjacent slender components such that each of the slender components is electrically isolated from the other slender components, the elongate member and longitudinal axis extending collinearly in a straight line along the primary central axis of the primary transmitter coil with the elongate member formed from a magnetically permeable material, the elongate member having:
e) a member length extending along the primary central axis above and below the primary coil height, and
f) an outer diameter along the length of the elongate member, wherein the outer diameter of the elongate member is smaller than the primary minimum diameter of the primary transmitter coil to define a ring shaped gap between the outer diameter of the elongate member and the primary transmitter coil;
iii) a power supply operably attached to the primary transmitter coil to energize the primary coil, wherein when the primary transmitter coil is energized, the primary transmitter coil is configured to generate a toroidal shaped electromagnetic energy field having a generally circular cross section rotated around the primary central axis of the primary transmitter coil and the elliptical cross section of the primary transmitter coil, and the elongate member is configured to reshape the circular cross section of the toroidal electromagnetic energy field by elongating the circular cross section into an elongated elliptical cross section having an elongated major axis parallel to the primary central axis of the primary transmitter coil, and by moving the elliptically elongated electromagnetic field farther away from the surface of the primary coil in directions along the major axis;

an internal device configured to be implanted beneath the skin of a patient and to inductively receive electromagnetic energy transmitted from the external device, the internal device comprising:
iv) a secondary receiver coil comprising at least one wire wrapped around a secondary central axis of the secondary receiver coil into a toroid shape encircling the secondary central axis, the toroid shape having:
g) an exterior secondary surface defined by an elliptical cross section of the toroid shape rotated about the secondary central axis of the secondary receiver coil, and
h) a secondary central gap between the secondary surface and the secondary central axis,
v) an implant circuit attached to the secondary receiver coil to receive energy inductively transmitted from the primary receiver coil, wherein when the implant circuit and the secondary receiver coil are implanted at a depth below the patients skin with the central axis of the secondary receiver coil oriented perpendicular to the patients skin, and primary transmitter coil is placed outside of the patient's skin with the primary central axis coaxially aligned with the secondary central axis of the secondary receiver coil, and the primary transmitter coil is energized to inductively transfer energy directly to the secondary receiver coil, the configuration of the primary transmitter coil with the elongate member generates an elliptically elongated toroidal electromagnetic energy field around the surface of the primary transmitter coil that is elliptically elongated in a direction to penetrate into the patient's skin, wherein when the secondary receiver coil inductively receives energy from the elongated toroidal electromagnetic energy field transmitted directly from the primary transmitter coil, the inductive energy transfer is optimized by the elongation of the toroidal electromagnetic energy field to maximize the power transmission between the internal device and the external device and to maximize the implant depth for operative transfer of energy from the external device to the internal device.

2. The transcutaneous energy transfer device of claim 1, wherein the elongate member comprises a ferrite material.

3. The transcutaneous energy transfer device of claim 2, wherein the elongate member comprises a rod.

4. The transcutaneous energy transfer device of claim 2, further comprising a magnetic shield comprising a backplane attached to the elongate member and covering a side of the primary coil opposite to the secondary coil.

5. The transcutaneous energy transfer device of claim 4, wherein the magnetic shield further comprises a cylindrical flange attached and inwardly directed from the backplane to define a ring groove to receive the primary coil.

6. The transcutaneous energy transfer device of claim 1, wherein the elongate member comprises an elongate rod that has a length of between about one inch and four inches.

7. The transcutaneous energy transfer device of claim 6, wherein the elongate member comprises a rod having a length of about three inches and a diameter of about three-quarter inches.

8. The transcutaneous energy transfer device of claim 7, wherein the elongate member comprises a ferrite material.

9. The transcutaneous energy transfer device of claim 1, wherein the plurality of slender components are formed from steel.

10. The transcutaneous energy transfer device of claim 1, wherein the plurality of slender components are formed from ferrite.

11. A transcutaneous energy transfer device for transferring energy from an external device located outside of a patient's skin to an internal device implanted below the patient's skin, the transcutaneous energy transfer device comprising:

an external primary transmitter coil to which energy to be transferred is applied, wherein the external primary transmitter coil has an outer diameter, wherein the external primary transmitter coil comprises at least one wire wrapped around a primary central axis of the external primary transmitter coil into a toroidal shape encircling the primary central axis, the toroid shape having an elliptical cross section rotated about the primary central axis and defining a center gap, and having a primary minimum diameter where the primary surface of the toroid shape is closest to the primary central axis, wherein the toroid shape further defines a primary coil height, wherein the primary coil height is less than the primary minimum diameter;

an implanted secondary receiver coil comprising at least one wire wrapped around a secondary central axis of the secondary receiver coil into a toroid shape encircling the secondary central axis, wherein the toroid shape of the implanted secondary receiver coil defines an exterior secondary surface defined by an elliptical cross section of the toroid shape rotated about the secondary central axis of the secondary transmitter coil, and further defines a secondary central gap between the secondary surface and the secondary central axis, wherein the implanted secondary coil is configured to be inductively coupled to the external primary transmitter coil when the primary coil is placed adjacent to the skin and the secondary central axis is coaxially aligned with the primary central axis, wherein when the implanted secondary receiver coil is connected to a subcutaneous utilization device, wherein the inductively coupled energy is conducted to the subcutaneous utilization device; and a slender cylindrical member centered within the center gap of the external primary transmitter coil member, the slender cylindrical member defining a longitudinal axis coaxially aligned with the primary center axis of the external primary transmitter coil, the slender cylindrical member extending above and below the external primary transmitter coil height and having a uniform outer diameter that is smaller than a diameter of the center gap of the external primary transmitter coil member to define a ring shaped gap between the primary surface of the external primary transmitter coil and the outer diameter of the slender cylindrical member, the slender cylindrical member being formed from a ferrite material, wherein the outer diameter of the slender cylindrical member is less than or equal to one fourth of the outer diameter of the external primary transmitter coil;

wherein when the longitudinal axis of the slender cylindrical member and the primary central axis and the secondary central axis of both the external primary transmitter coil and the implanted secondary receiver coil are all coaxially aligned on opposite sides of the patient's skin and the external primary transmitter coil is energized, the external primary transmitter coil is configured to generate a toroidal electromagnetic energy field having a generally circular cross section rotated around the primary central axis of the primary transmitter coil and the elliptical cross section of the primary transmitter coil to inductively transfer energy directly to the implanted secondary coil, wherein the elongate member is configured to elongate the circular cross section of the toroidal electromagnetic energy field into an elongated elliptical cross section having an elongated major axis parallel to the longitudinal axis and configured to move the elliptically elongated electromagnetic field farther away from the surface of the external primary transmitter coil, wherein the inductive energy transfer is optimized by the elongation of the toroidal electromagnetic energy field to maximize the power transmission between the internal device and the external device and to maximize the implant depth for operative transfer of energy from the external device to the internal device.

12. A transcutaneous energy transfer device for inductively coupling energy from an external device to an internal device configured to apply energy to a subcutaneous utilization device, the transcutaneous energy transfer device comprising:

an external primary transmitter coil to which energy to be transferred is applied, wherein the external primary transmitter coil comprises at least one wire wrapped around a primary central axis of the primary transmitter coil into a toroidal shape encircling the primary central axis, the toroid shape having an elliptical cross section rotated about the primary central axis, and defining a center gap and a primary minimum diameter where the primary surface of the toroid shape is closest to the primary central axis, wherein the external annular primary coil member further defines a primary coil height and the primary coil height is less than the primary minimum diameter;

a pot core comprising a disk portion and a cylindrical flange, wherein the pot core defines a central axis coaxially aligned with the primary central axis of the primary transmitter coil, wherein the cylindrical flange extends transversely relative to a first face of the disk portion, wherein the cylindrical flange has an inner surface and an outer surface, the pot core further comprising an elongated member, wherein the elongated member extends transversely relative to a first face of the disk portion, wherein the external primary transmitter coil is positioned closer to the inner surface of the cylindrical flange than the external primary transmitter coil is to the elongated member, wherein the elongated member is centered within the circular center gap of the external primary transmitter coil and is formed from a magnetically permeable material, wherein the elongated member defines a longitudinal axis coaxially aligned with the primary central axis of the external primary transmitter coil and the central axis of the pot core, the elongated member having a uniform diameter that is smaller than a diameter of the center gap of the external primary transmitter coil, wherein the elongated member defines a ring shaped center gap between the external primary transmitter coil and the elongated member, wherein the ring shaped center gap between the external primary transmitter coil and the elongated member defines a lateral distance between the external primary transmitter coil and the elongated member, wherein the lateral distance between the external primary transmitter coil and the elongated member is greater than a lateral distance between the external primary transmitter coil and the inner surface of the cylindrical flange, wherein the elongate member is configured to deform a circular cross sectional toroidal electromagnetic field generated by the external primary transmitter coil into an elliptical cross sectional toroidal electromagnetic field, the elliptical cross section of the field having an elongated major axis parallel to the primary central axis of the external primary transmitter coil to thereby move the elliptically elongated electromagnetic field farther away from the surface of the external primary transmitter coil in directions along the major axis;

an implanted secondary receiver coil comprising at least one wire wrapped around a secondary central axis of the implanted secondary receiver coil into a toroid shape encircling the secondary central axis, wherein the toroid shape of the implanted secondary receiver coil has an exterior secondary surface defined by an elliptical cross section of the toroid shape rotated about the secondary central axis of the implanted secondary receiver coil, wherein the toroid shape defines a secondary central gap between the secondary surface and the secondary central axis; and excitation circuitry operatively configured to selectively energize the external primary transmitter coil to create an elliptical toroidal electromagnetic field to inductively couple energy directly from the external primary transmitter coil to the implanted secondary receiver coil when the primary central axis and the secondary central axis of the respective external primary transmitter coil and the implanted secondary receiver coil are coaxially aligned, wherein the inductive energy transfer is optimized by the elongation of the toroidal electromagnetic energy field to maximize the power transmission between the internal device and the external device and to maximize the implant depth for operative transfer of energy from the external device to the internal device.

* * * * *